United States Patent
Wang et al.

(10) Patent No.: US 11,999,995 B2
(45) Date of Patent: Jun. 4, 2024

(54) METHYLOME PROFILING IN ANIMALS AND USES THEREOF

(71) Applicant: The Regents of the University of California, Oakland, CA (US)

(72) Inventors: Tina Wang, San Diego, CA (US); Trey Ideker, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/638,454

(22) PCT Filed: Aug. 31, 2018

(86) PCT No.: PCT/US2018/049103
§ 371 (c)(1),
(2) Date: Feb. 11, 2020

(87) PCT Pub. No.: WO2019/046725
PCT Pub. Date: Mar. 7, 2019

(65) Prior Publication Data
US 2020/0362402 A1   Nov. 19, 2020

Related U.S. Application Data (60) Provisional application No. 62/553,115, filed on Aug. 31, 2017.

(51) Int. Cl.
C12Q 1/68        (2018.01)
C12Q 1/6855      (2018.01)
C12Q 1/686       (2018.01)

(52) U.S. Cl.
CPC ........... *C12Q 1/6855* (2013.01); *C12Q 1/686* (2013.01); *C12Q 2523/125* (2013.01); *C12Q 2535/122* (2013.01); *C12Q 2537/143* (2013.01); *C12Q 2600/154* (2013.01)

(58) Field of Classification Search
CPC ...................................................... C12Q 1/68
USPC .................................................................. 435/6
See application file for complete search history.

(56) References Cited

U.S. PATENT DOCUMENTS

2015/0259742 A1   9/2015  Zhang et al.
2016/0222448 A1   8/2016  Horvath

FOREIGN PATENT DOCUMENTS

WO   2018/146482 A1   8/2018

OTHER PUBLICATIONS

Stubbs et al. (Multi-tissue DNA methylation age predictor in mouse, Genome Biol. Apr. 11, 2017;18(1):68. doi: 10.1186/s13059-017-1203-5).*
Petkovich et al. (Using DNA Methylation Profiling to Evaluate Biological Age and Longevity Interventions, Cell Metab. Apr. 4, 2017;25(4):954-960.e6. doi: 10.1016/j.cmet.2017.03.016).*
Tang, Xiaofan, International Preliminary Report on Patentability and Written Opinion, PCT/US2018/049103, The International Bureau of WIPO, dated Mar. 12, 2020.

(Continued)

*Primary Examiner* — Aaron A Priest
(74) *Attorney, Agent, or Firm* — Mintz, Levin, Cohn, Ferris, Glovsky and Popeo, P.C.

(57) ABSTRACT

The disclosure provides for methylome profiling of animals and further using DNA methylation as a quantitative predictor of the age of an animal.

2 Claims, 5 Drawing Sheets

(56) References Cited

OTHER PUBLICATIONS

Illumina, TruSeq Methyl Capture EPIC Library Prep Kit, 2016, Retrieved Dec. 11, 2018, URL:https://www.illumina.com/content.dam/illumina-marketing/documents/products/datasheets/truseq-methyl-capture-epic-sequencing-panel-data-sheet-470-2016-004.pdf.
Wang et al., "Epigenetic aging signatures in mice livers are slowed by dwarfism, calorie restriction and rapamycin treament", Genome Biol., Mar. 28, 2017, vol. 18, No. 1, pp. 1-11.
Young, Lee W., International Search Report and Written Opinion, PCT/US2018/049103, United States Patent and Trademark Office, dated Dec. 28, 2018.

* cited by examiner

METHYLOME PROFILING IN ANIMALS AND USES THEREOF

CROSS REFERENCE TO RELATED APPLICATIONS

This application is a U.S. National Stage Application filed under 35 U.S.C. § 371 and claims priority to International Application No. PCT/US2018/049103, filed Aug. 31, 2018, which claims priority under 35 U.S.C. § 119 from Provisional Application Ser. No. 62/553,115, filed Aug. 31, 2017, the disclosures of which are incorporated herein by reference.

STATEMENT OF GOVERNMENT SUPPORT

This invention was made with Government support under Grant No. GM008666, awarded by the National Institutes of Health. The Government has certain rights in the invention.

TECHNICAL FIELD

The disclosure provides for methylome profiling of animals and further provides for the use of DNA methylation as a quantitative predictor of the age of an animal.

BACKGROUND

Changes in cellular genetic information, such as mutations in gene sequences which can affect gene expression and/or protein sequence, are associated with many diseases and conditions. However, changes can also occur to genes that affect gene expression; changes caused by mechanisms other than genetic mutations.

Epigenetics is the study of changes in gene expression caused by mechanisms other than changes in the underlying DNA sequence, the methylation of DNA being one of those mechanisms. Methylation of DNA refers to the addition of a methyl group to the 5 position of a cytosine pyrimidine ring or the positional sixth nitrogen of an adenine purine ring. Methylation of DNA plays a critical role in the regulation of gene expression in development and differentiation of diseases such as multiple sclerosis, diabetes, schizophrenia, aging, and cancers. In adult somatic cells, DNA methylation typically occurs in regions where a cytosine nucleotide (C) is found next to a guanine nucleotide (G) where the C and G are linked by a phosphate group (p), the linear construct being referred to as a "CpG" site. Methylation in particular gene regions, for example, in gene promoter regions, can augment or inhibit the expression of these genes.

In vertebrates, the DNA methylation pattern is established early in embryonic development and in general the distribution of 5-methylcytosine (5 mC) along the chromosome is maintained during the life span of the organism. Stable transcriptional silencing is important for normal development, and is associated with several epigenetic modifications. If methylation patterns are not properly established or maintained, various disorders like mental retardation, immune deficiency and sporadic or inherited cancers may follow.

SUMMARY

Provided herein is custom assay to interrogate a non-human subject's methylome (e.g., a canine methylome) as well as age-related methylation activity. This assay targets orthologous sequence regions between an animal subject and humans, to identify regions that are important for methylation changes in both species.

In the experiments presented herein, orthologous regions in a non-human genome are identified on a human methylation chip (e.g., Illumina 450K methylation chip). More than 129,000 regions were targeted in the human that were orthologous to regions in dogs, yielding ~18.8 MB of targeted sequence across 113,007 unique regions. These targeted sequences were captured using a custom oligonucleotide library which were synthesized using the Roche NimbleGen SeqCap system.

Additionally provided herein are methods to quantitatively measure the age of an animal subject based upon the methylation status of select epigenetic predictors. The methods disclosed herein are particularly useful for determining the age of dogs and cats which were adopted from shelters, which is the case for the vast majority of dogs and cats in the United States and other developed countries. This technology is of use for owners and pet insurance providers as age is predictive of health-related issues that typically arise in cats and dogs. Further, the methods disclosed herein could also be used to assess the 'aging rate' of animal subject, thereby further predicting health-related issues that typically arise in cats and dogs as they age.

In a particular embodiment, the disclosure provides a method to create a methylome profile of a mammalian animal subject, comprising: extracting and quantifying DNA from the blood of a mammalian animal subject, wherein the mammalian animal subject is not a human or mouse; preparing a whole-genome-bisulfite library preparation using the extracted DNA from the one or more animal subjects; hybridizing the whole-genome-bisulfite library preparation to capture probes; mass sequencing successfully captured libraries to create sequencing reads; and analyzing the sequencing reads using Bowtie2 that is specialized for bisulfite conversion so as to create a methylome profile of the animal subject. In a further embodiment, the mammalian animal subject is selected from the group consisting of dogs, cats, horses, cattle, bison, deer, elk, reindeer, pigs, goats, sheep, zebu, guinea pigs, donkeys, mules, water buffalo, camels, yak, llamas, alpacas, ferrets, gayal, rabbits, rats, minks, and hedgehogs. In a further embodiment, the mammalian animal subject is selected from the group consisting of dog, cat, and horse. In a certain embodiment, the mammalian animal subject is a dog.

In a particular embodiment, preparing a whole-genome-bisulfite library preparation comprises: shearing the extracted DNA to 100-500 bp fragments; ligating methylated sequencing adapters; and treating the ligated DNA with bisulfite to create the whole-genome-bisulfite library preparation. In a further embodiment, successfully captured libraries are sequenced by first PCR amplified using the ligated methylated sequencing adapters, and sequencing with 2×100 bp reads on an Illumina HiSeq 4000, to generate at least 100 million sequencing reads.

In a certain embodiment, a methylome profile of the mammalian animal subject described herein comprises a coverage of at least 100,000 CpG sites. In a further embodiment, a methylome profile of the mammalian animal subject described herein comprises about ~2.9 million CpG sites.

In a particular embodiment, the disclosure also provides a method to predict the age of a mammalian animal subject, comprising: creating a syntenic set of CpGs that are present both in a human and the mammalian animal subject; training a predictor of age using dog methylation data using a machine learning framework; selecting parameters using k-fold cross-validation, and testing against a with-held test cohort of dog subjects to generate a validated epigenetic predictor. In a further embodiment, the machine learning framework is an ElasticNet regression framework. In another embodiment, the disclosure provides an alternate method to predict the age of a mammalian animal subject, comprising: training a predictor of age using methylation data created by methylome profiling a population of mammalian animals using a machine learning framework, wherein the mammalian animal subject is same type of animal as the population mammalian animals; selecting parameters using k-fold cross-validation, and testing against another cohort of mammalian animals to generate a validated epigenetic predictor; and applying the validated epigenetic predictor against a methylome profile of the animal subject to predict the age of the animal subject. In a further embodiment, the machine learning framework is an ElasticNet regression framework. In yet a further embodiment, the mammalian animal subject is selected from the group consisting of dogs, cats, horses, cattle, bison, deer, elk, reindeer, pigs, goats, sheep, zebu, guinea pigs, donkeys, mules, water buffalo, camels, yak, llamas, alpacas, ferrets, gayal, rabbits, rats, minks, and hedgehogs. In another embodiment the mammalian animal subject is selected from the group consisting of dog, cat, and horse. In a certain embodiment, the mammalian animal subject is a dog.

In a particular embodiment, the disclosure also provides for a methylation bead chip comprising a panel of 100-400 CpG sites which methylation status are a quantitative predictor of age of a mammalian animal subject, wherein the mammalian animal subject is not a human. In a further embodiment, the mammalian animal subject is selected from the group consisting of dogs, cats, horses, cattle, bison, deer, elk, reindeer, pigs, goats, sheep, zebu, guinea pigs, donkeys, mules, water buffalo, camels, yak, llamas, alpacas, ferrets, gayal, rabbits, rats, minks, and hedgehogs. In yet a further embodiment, the mammalian animal subject is selected from the group consisting of dog, cat, and horse. In another embodiment, the mammalian animal subject is a dog.

DETAILED DESCRIPTION

As used herein and in the appended claims, the singular forms "a," "an," and "the" include plural referents unless the context clearly dictates otherwise. Thus, for example, reference to "an animal subject" includes a plurality of such animal subjects and reference to "the profile" includes reference to one or more profiles and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated herein by reference in full for the purpose of describing and disclosing the methodologies, which might be used in connection with the description herein. Moreover, with respect to any term that is presented in one or more publications that is similar to, or identical with, a term that has been expressly defined in this disclosure, the definition of the term as expressly provided in this disclosure will control in all respects.

The term "age-controlled non-human mammalian methylation profile" refer to a methylome profile from a control animal having a known date of conception or birth (i.e., a chronological age) having had its methylome determined to provide a methylome profile based upon its chronological age. The age-controlled non-human mammalian methylation profile can be obtained from an organism through tissue or biopsy samples at varying points during its life time (e.g., birth, 1 month, 2 months, 6 months, 1 year, 2 years etc. until natural death).

The term "array" or "microarray" as used herein refers to an intentionally created collection of molecules which can be prepared either synthetically or biosynthetically (e.g. Illumina® Infinium® HumanMethylation27 microarrays). The molecules in the array can be identical or different from each other. The array can assume a variety of formats, for example, libraries of soluble molecules; libraries of compounds tethered to resin beads, silica chips, or other solid supports.

As used herein, the biological age (bioage), chemical age, methylomic age and molecular age are equivalent or synonymous. The biological age is determined using a set of age-associated epigenetic markers of a subject or an organism. The biological age is determined from an analysis of the modification status of specific CpG dinucleotide and, in particular, e.g., the methylation status at the C-5 position of cytosine.

Chronological age is the actual age of a subject or organism. For animals and humans, chronological age may be based on the age calculated from the moment of conception or based on the age calculated from the time and date of birth. The chronological age of the cell, tissue or organ may be determined from the chronological age of the subject or organism from which the cell, tissue or organ is obtained, plus the duration of the cell, tissue or organ is placed in culture. Alternatively, in the case of the cell or tissue culture, the chronological age may be related to the total or accumulative time in culture or passage number.

As used herein, the term "cell-free," when used in reference to DNA, is intended to mean DNA (e.g., cfDNA; cell-free DNA) that has been removed from a cell. Cell-free DNA refers to DNA molecules of 25 nucleotides or longer that are not contained within any intact cells. The removal of the DNA can be a natural process such as necrosis or apoptosis. Cell-free DNA is generally obtained from blood, or a fraction thereof, such as plasma. Cell-free DNA can be obtained from other bodily fluids or tissues.

As used herein, the term "cell type" is intended to identify cells based on morphology, phenotype, developmental origin or other known or recognizable distinguishing cellular characteristic. A variety of different cell types can be obtained from a single organism (or from the same species of organism). Exemplary cell types include, but are not limited to urinary bladder, pancreatic epithelial, pancreatic alpha, pancreatic beta, pancreatic endothelial, bone marrow lymphoblast, bone marrow B lymphoblast, bone marrow macrophage, bone marrow erythroblast, bone marrow dendritic, bone marrow adipocyte, bone marrow osteocyte, bone marrow chondrocyte, promyeloblast, bone marrow megakaryoblast, bladder, brain B lymphocyte, brain glial, neuron, brain astrocyte, neuroectoderm, brain macrophage, brain microglia, brain epithelial, cortical neuron, brain fibroblast, breast epithelial, colon epithelial, colon B lymphocyte, mammary epithelial, mammary myoepithelial, mammary fibroblast, colon enterocyte, cervix epithelial, ovary epithelial, ovary fibroblast, breast duct epithelial, tongue epithelial, tonsil dendritic, tonsil B lymphocyte, peripheral blood lymphoblast, peripheral blood T lymphoblast, peripheral blood cutaneous T lymphocyte, peripheral blood natural killer, peripheral blood B lymphoblast, peripheral blood monocyte, peripheral blood myeloblast, peripheral blood monoblast, peripheral blood promyeloblast, peripheral blood macrophage, peripheral blood basophil, liver endothelial, liver mast, liver epithelial, liver B lymphocyte, spleen endothelial, spleen epithelial, spleen B lymphocyte, liver hepatocyte, liver Alexander, liver fibroblast, lung epithelial, bronchus epithelial, lung fibroblast, lung B lymphocyte, lung Schwann, lung squamous, lung macrophage, lung osteoblast, neuroendocrine, lung alveolar, stomach epithelial and stomach fibroblast. For purposes of comparison, a first cell is a human cell that is compared to a second cell that is from a non-human subject (e.g., a cell from a canine).

As used herein, the term "circulating," when used in reference to DNA, is intended to mean DNA that is or was moving through the circulatory system of an organism, whether in cell-free form or inside circulating cells.

As used herein, the term "coverage," when used in reference to a genetic locus, is intended to mean the number of detection events (e.g., sequence reads) that align to, or "cover," the locus. In some embodiments, the term refers to the average number of detection events (e.g., sequence reads) that align to, or "cover," a plurality of loci. Generally, the coverage level obtained from a sequencing method correlates directly with the degree of confidence in the accuracy of the call (e.g., nucleotide type or methylation state) determined at a particular base position or genetic locus. At higher levels of coverage, a locus is covered by a greater number of aligned sequence reads, so calls can be made with a higher degree of confidence.

As used herein, the term "CpG site" is intended to mean the location in a nucleic acid molecule, or sequence representation of the molecule, where a cytosine nucleotide and guanine nucleotide occur, the 3' oxygen of the cytosine nucleotide being covalently attached to the 5' phosphate of the guanine nucleotide. The nucleic acid is typically DNA. The cytosine nucleotide can optionally contain a methyl moiety, hydroxymethyl moiety or hydrogen moiety at position 5 of the pyrimidine ring. CpG site is used interchangeable with "methylation site".

As used herein, the term "derived," when used in reference to DNA, is intended to refer to the source from which the DNA was obtained or the origin where the DNA was synthesized. In the case of biologically derived DNA, the term can be used to refer to an in vivo source from which the DNA was obtained or the in vivo origin where the DNA was synthesized. Exemplary origins include, but are not limited to, a cell, cell type, tissue, tissue type, organism or species of organism. In the case of synthetically derived DNA, the term can be used to refer to an in vitro source from which the DNA was obtained or the in vitro origin where the DNA was synthesized. A DNA molecule that is derived from a particular source or origin can nonetheless be subsequently copied or amplified. The sequence of the resulting copies or amplicons can be referred to as having been derived from the source or origin.

As used herein, the term "each," when used in reference to a collection of items, is intended to identify an individual item in the collection but does not necessarily refer to every item in the collection. Exceptions can occur if explicit disclosure or context clearly dictates otherwise.

The term "epigenetic" refers to or involves a modification in gene expression that is independent of DNA sequence. Epigenetic factors include modifications in DNA methylation and chromatin structure.

As used herein, the term "methylation difference" is intended to mean a qualitative or a quantitative indicium that two nucleotides or nucleic acids do not have the same methylation state. The methylation difference can be indicated for nucleotides that are at aligned positions on different nucleic acids. In some cases, the methylation difference can be a sum or aggregate of a plurality of aligned positions. When two or more nucleic acids are aligned, the methylation difference can be an average across one or more aligned positions.

The term "methylation marker" as used herein refers to a CpG position that is potentially methylated. Methylation typically occurs in a CpG containing nucleic acid sequence. The CpG containing nucleic acid may be present in, e.g., in a CpG island, a CpG doublet, a promoter, an intron, or an exon of gene. For instance, in the genetic regions provided herein the potential methylation sites encompass the promoter/enhancer regions of the indicated genes. Thus, the regions can begin upstream of a gene promoter and extend downstream into the transcribed region.

As used herein, the term "methylation state," when used in reference to a locus (e.g., a CpG site or polynucleotide segment) across several molecules having that locus, refers to one or more characteristics of the locus relevant to presence or absence of a methyl moiety. Non-limiting examples of such characteristics include whether any of the cytosine (C) bases within a locus are methylated, location of methylated C base(s), percentage of methylated C base(s) at a particular locus, and allelic differences in methylation due to, for example, difference in the origin of alleles. Reference to the methylation state of a particular CpG site in a nucleic acid molecule, is directed to the presence or absence of a methyl moiety at position 5 of the pyrimidine ring of a cytosine. The term can be applied to one or more cytosine nucleotides (or representations thereof e.g. a chemical formula), or to one or more nucleic acid molecules (or representations thereof, e.g., a sequence representation). The term can also refer to the relative or absolute amount (e.g., concentration) of methylated C or non-methylated C at a particular locus in a nucleic acid. A methylation state sometimes is hypermethylated and sometimes is hypomethylated. For example, if all or a majority of C bases within a locus are methylated, the methylation state can be referred to as "hypermethylated." In another example, if all or a majority of C bases within a locus are not methylated, the methylation state may be referred to as "hypomethylated." Likewise, if all or a majority of C bases within a locus are methylated as compared to reference then the methylation state is considered hypermethylated compared to the reference. Alternatively, if all or a majority of the C bases within a locus are not methylated as compared to a reference then the methylation state is considered hypomethylated compared to the reference.

A "methylation site" is a locus in a nucleic acid where methylation has occurred, or has the possibility of occurring. A methylation site sometimes is a C base, or multiple C bases in a region, and sometimes a methylation site is a CpG site in a locus. Each methylation site in the locus may or may not be methylated. A methylation site can be susceptible to methylation by a naturally occurring event in vivo or by an event that chemically methylates a nucleotide in vitro.

The term "methylome" refers to a set of methylation modifications (e.g., at methylation sites) in an organism's genome. The disclosure includes age-associated methylomes. In one embodiment, the age-associated methylome refers to a set of orthologous markers across a plurality of organisms that have conserved methylation sites associated with genetic loci.

As used herein, the term "mixture," when used in reference to two or more components, is intended to mean that the two or more components are simultaneously present in a fluid or vessel. The components are typically capable of contacting each other via diffusion or agitation. The components may be separate molecules (e.g., two or more nucleic acid fragments) or the components may be part of a single molecule (e.g., sequence regions on a long nucleic acid molecule).

The phrase "selectively measuring" as used herein refers to methods wherein only a finite number of methylation marker or genes (comprising methylation markers) are measured rather than assaying essentially all potential methylation marker (or genes) in a genome. For example, in some aspects, "selectively measuring" methylation markers or genes comprising such markers can refer to measuring no more than 10,000, 1,000, 900, 800, 700, 600, 500, 400 or 300 different methylation markers or genes comprising methylation markers.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

As used herein, the term "tissue" is intended to mean a collection or aggregation of cells that act together to perform one or more specific functions in an organism. The cells can optionally be morphologically similar. Exemplary tissues include, but are not limited to, eye, muscle, skin, tendon, vein, artery, blood, heart, spleen, lymph node, bone, bone marrow, lung, bronchi, trachea, gut, small intestine, large intestine, colon, rectum, salivary gland, tongue, gall bladder, appendix, liver, pancreas, brain, stomach, skin, kidney, ureter, bladder, urethra, gonad, testicle, ovary, uterus, fallopian tube, thymus, pituitary, thyroid, adrenal, or parathyroid. Tissue can be derived from any of a variety of organs of an animal.

Currently, the accepted method to estimate age in domesticated animals, like dogs, cats and livestock, is based on the quality of teeth. However, this method of estimating age is error-prone for these animals. For example, estimating age based on quality of teeth or ocular features, has an accuracy rate of ~50% at best for domesticated pets. In regards to age prediction using methylation status, studies have shown that it is possible to build accurate predictors for age in humans, which are known as 'epigenetic-age predictors'. While the studies described herein are described in certain mammalian organisms (e.g., dogs), other mammalian organisms can be similarly analyzed (e.g., equines, porcine, bovines, felines etc.). It was postulated herein that age-related methylome changes would be conserved in mammals, and that these 'conserved' changes could be used to determine age in mammalian species in addition to humans and primates.

DNA methylation data can provide valuable information, when evaluated independently or in combination with other information such as genotype or gene expression patterns. One object of the methods set forth herein is to determine this information, e.g., if one or more sites in a genome are differentially methylated in a test sample compared to a reference sample or data set.

Particular embodiments can be used for the detection, screening, monitoring (e.g., for relapse, remission, or response to treatment), staging, classification (e.g., for aid in choosing the most appropriate treatment modality) and prognostication of an animals' age using methylation analysis of circulating plasma/serum DNA.

Current studies do not allow sufficient coverage for methylation status comparisons between humans (extensively studied) vs., non-human mammals such as canines (poorly studied). Existing methods cannot reliably capture a large number of overlapping sites without extensive mass sequencing. While reduced representation bisulfite sequencing (RRBS) is very popular method to study non-human organisms that do not have arrays readily available, sequencing depth severely limits the number of individuals that can be sampled.

In direct contrast to the current studies, the methods disclosed herein target orthologous regions in animals and provides methylation status via bisulfite-treatment, thereby capturing selected regions. The captured selected regions can then be sequenced. As shown herein, a targeted-methylome profiling assay (Roche Nimblegen SeqCap-Epi) was reproducibly used to measure the methylation status at defined regions in a large number of animal subjects. The platform technologies of the disclosure allow for the training of diagnostic models that can be used to predict age in animal subjects (e.g., dogs) using their DNA methylome. By leveraging the DNA methylome techniques described herein, quantitative measure of various conditions in subjects, such as age, can be performed.

Orthologous regions can be identified using methylome chips (e.g., Illumina 450K chips). For example, canine orthologs for age-dependent methylome analysis can be identified by contacting a human chip (e.g., Illumina 450K chip) with DNA from a canine. Orthologous sites will bind the DNA from the canine animal. These orthologs can then be identified and their sequences provided on a specific "canine chip". This process can be repeated for various organisms to provide a library of age-related methylome orthologs. For example, using such a method a plurality of age-related methylome genetic locations were identified in canines. These age-related methylome genetic loci are provided in Table 1.

TABLE 1

Canine age-related methylome markers

| chromosome | Genomic location | |
| --- | --- | --- |
| | start | end |
| 10 | 32155572 | 32155573 |
| 10 | 47400603 | 47400604 |
| 11 | 12143642 | 12143643 |
| 1 | 113745958 | 113745959 |
| 11 | 56810628 | 56810629 |
| 11 | 56810721 | 56810722 |
| 12 | 63488774 | 63488775 |
| 14 | 22067955 | 22067956 |
| 14 | 40131029 | 40131030 |
| 14 | 40366402 | 40366403 |
| 16 | 46562076 | 46562077 |
| 16 | 53697863 | 53697864 |
| 16 | 53697881 | 53697882 |
| 17 | 62480024 | 62480025 |
| 21 | 27195140 | 27195141 |
| 21 | 27396898 | 27396899 |
| 22 | 1780265 | 1780266 |
| 23 | 42484424 | 42484425 |
| 24 | 36795647 | 36795648 |
| 25 | 5057162 | 5057163 |
| 25 | 5057174 | 5057175 |
| 26 | 5250703 | 5250704 |
| 26 | 5330973 | 5330974 |
| 26 | 5330978 | 5330979 |
| 26 | 5330998 | 5330999 |
| 26 | 5331204 | 5331205 |
| 26 | 5331230 | 5331231 |
| 28 | 38491744 | 38491745 |
| 30 | 14008101 | 14008102 |
| 3 | 15906095 | 15906096 |
| 3 | 15906160 | 15906161 |
| 32 | 30355909 | 30355910 |
| 33 | 25412867 | 25412868 |
| 34 | 7326879 | 7326880 |
| 37 | 22520990 | 22520991 |
| 38 | 18152079 | 18152080 |
| 38 | 18152126 | 18152127 |
| 38 | 18152133 | 18152134 |
| 5 | 29282901 | 29282902 |
| 5 | 32970662 | 32970663 |
| 5 | 32970672 | 32970673 |
| 5 | 48883108 | 48883109 |
| 5 | 48883118 | 48883119 |
| 5 | 67246847 | 67246848 |
| 5 | 79537151 | 79537152 |
| 7 | 80969482 | 80969483 |
| 9 | 19960393 | 19960394 |
| 9 | 20510871 | 20510872 |
| 9 | 24868907 | 24868908 |
| 9 | 24868926 | 24868927 |
| 9 | 24869027 | 24869028 |

Based upon the foregoing genetic loci, primers and/or probes can be designed. Such primers and/or probes will be of sufficient length (e.g., about 18-30 bp) to allow hybridization and/or amplification of the cited genomic locus.

Thus, the disclosure provides a method comprising isolating genomic DNA (gDNA) from a non-human mammalian animal species, identifying regions that are conserved regions with humans to generate an orthologous methylome profile of the non-human mammalian animal species; measuring the methylation profile of an orthologous methylome profile of the non-human mammalian animal species; and determining the age of the non-human mammalian animal species by comparing the methylation profile to an age-controlled non-human mammalian methylation profile from the same species. In on embodiment, the non-human mammalian animal species is a canine. In a further embodiment, the methylome profile comprises from 1-10,000 orthologous methylation sites. In still a further embodiment, the method comprises from 1-51 (and any whole number there between), e.g., 1-2, 3-4, 5-10, 10-20, 20-30, 30-40, 40-51 genetic loci/methylation sites of Table 1.

In a particular embodiment, the methods of the disclosure can be used to significantly reduce measurement error in determining the age of an animal subject. Accordingly, the methods of the disclosure will allow pet owners or pet insurance adjustors to better determine the actual age of animal subject, which can be used to predict future medical expenses and make informed decisions as to current medical treatment of the animal subject. Thus, the methods disclosed herein can inform animal owners of the age of an adopted pet, such as a pet adopted from shelters, where prior life history is typically not known. Proper age estimation of these pets is important because age often plays a significant role when making medical decisions for their pets. Estimating age based on tooth-wear (the commonly used metric in shelters) is very inaccurate after the teeth have fully erupted, generally by 6-7 months of age in dogs. Thus, shelters commonly underestimate the ages of animals so as to increase the likelihood that the animals will be adopted, as people generally have a preference for younger pets. Thus, the methods and technology presented herein, provide a quantitative metric in order to evaluate the age of the animal subject, thereby allowing a potential animal owner or pet insurance adjustor to have a better idea of the animal's age and possible risks of future medical issues. Moreover, repeated measures using the methods disclosed herein can be used to measure the 'aging rate' of the animal subject as they get older, to see if the animal is aging faster than expected.

Second, covariates can be taken from pets and their owners when ordering such an assay. Furthermore, repeated measures from owners that choose to monitor aging rate can further be used to assess covariates that affect aging (i.e., weight gain over time or presence of allergies). After enough pet owners have measured such an 'aging rate', this information could be sold to life insurance companies who are currently using human aging models to help them evaluate the epigenetic aging rates when calculating premiums for life and health insurance.

In further embodiments described herein, the methods disclosed can be used for determining methylation patterns in an animal subject that can be used to monitor development of a fetus (e.g., to determine the presence or absence of a developmental abnormality) or to determine the presence of a particular disease or condition. In such cases the method can be carried out using a sample (e.g., blood, tissue or amniotic fluid) obtained from a pregnant female animal subject and the sample can be evaluated for methylation levels of fetal nucleic acids. A DNA methylation profile of placental tissues can be used to evaluate the pathophysiology of pregnancy-associated or developmentally-related diseases. Such information can be of great interest to people seeking to own an animal subjects that usually command a high price, e.g., racehorses.

Additionally, the methods disclosed herein can be used to obtain diagnostic or prognostic information for other conditions in animal subject. For example, liver tissue from an animal subject can be analyzed to determine a methylation pattern specific to the liver, which may be used to identify liver pathologies. Other tissues which can also be analyzed include brain cells, bones, the lungs, the heart, the muscles and the kidneys, etc. DNA can be obtained from blood samples and analyzed in a method set forth herein in order to determine the state of any of a variety of tissues that contribute DNA to the blood.

The methylation patterns of various tissues may change from time to time, e.g. as a result of development, aging, disease progression (e.g. inflammation, cancer or cirrhosis) or treatment. The dynamic nature of DNA methylation makes such analysis potentially very valuable for monitoring of physiological and pathological processes in animal subjects. For example, if one detects a change in the plasma methylation pattern of an animal subject compared to a baseline value obtained of the animal subject when it was healthy, one could then detect disease processes in organs that contribute plasma DNA.

The methods disclosed herein can be carried out for any of a variety of animal test subjects. For the purposes of the disclosure an "animal subject" includes mammalian subjects. In a particular embodiment, the "animal subject" is not a human and/or a mouse. In a further embodiment, the "animal subject" is a domesticated animal, livestock or a pet. Examples of domesticated animals, livestock and pets, include but are not limited to, dogs, cats, horses, cattle, bison, deer, elk, reindeer, pigs, goats, sheep, zebu, guinea pigs, donkeys, mules, water buffalo, camels, yak, llamas, alpacas, ferrets, gayal, rabbits, rats, minks, and hedgehogs. In another embodiment, the animal is a zoo animal including endangered mammals. In yet a further embodiment, the animal subject is a dog or a cat.

Particular embodiments of the methods set forth herein can be carried out using methylation states for a plurality of sites from test genomic DNA from an individual test animal. In some cases, the data is provided to an individual or system that carries out the method. Alternatively, embodiments of the methods can include one or more steps for detecting methylation states for a plurality of sites in a test genome.

Methylation of sites, such as CpG dinucleotide sequences, can be measured using any of a variety of techniques used in the art for the analysis of such sites. For example, methylation can be measured by employing a restriction enzyme based technology, which utilizes methylation sensitive restriction endonucleases for the differentiation between methylated and unmethylated cytosines. Restriction enzyme based technologies include, for example, restriction digest with methylation-sensitive restriction enzymes followed by nucleic acid sequencing (e.g., massively parallel or Next Generation sequencing), Southern blot analysis, real time PCR, restriction landmark genomic scanning (RLGS) or differential methylation hybridization (DMH).

Restriction enzymes characteristically hydrolyze DNA at and/or upon recognition of specific sequences or recognition motifs that are typically between 4- to 8-bases in length. Among such enzymes, methylation sensitive restriction enzymes are distinguished by the fact that they either cleave, or fail to cleave DNA according to the cytosine methylation state present in the recognition motif of, e.g., the CpG sequences. In methods employing such methylation sensitive restriction enzymes, the digested DNA fragments can be differentially separated (e.g., based on size or hybridization affinity to complementary probes), differentially amplified (e.g., based on affinity to an amplification primer), or differentially detected (e.g., via a microarray detection technique or nucleic acid sequencing technique) such that the methylation status of the sequence can thereby be deduced.

In some embodiments that employ methylation sensitive restriction enzymes, a post-digest PCR amplification step is added wherein a set of two oligonucleotide primers, one on each side of the methylation sensitive restriction site, is used to amplify the digested genomic DNA. PCR products are produced and detected for templates that were not restricted (e.g., due to presence of a methylated restriction site) whereas PCR products are not produced where digestion of the subtended methylation sensitive restriction enzyme site occurs. Techniques for restriction enzyme based analysis of genomic methylation are known in the art and include the following: differential methylation hybridization (DMH) (Huang et al., 1999, *Human Mol. Genet.* 8, 459-70); Not I-based differential methylation hybridization (for example, WO02/086163A1); restriction landmark genomic scanning (RLGS) (Plass et al., 1999, Genomics 58:254-62); methylation sensitive arbitrarily primed PCR (AP-PCR) (Gonzalgo et al., 1997, Cancer Res. 57: 594-599); methylated CpG site amplification (MCA) (Toyota et. al., 1999, Cancer Res. 59: 2307-2312). Other useful methods for detecting genomic methylation are described, for example, in US Patent Application publication 2003/0170684 A1 or WO 04/05122. The references cited above are incorporated herein by reference.

Methylation of CpG dinucleotide sequences can also be measured by employing cytosine conversion based technologies, which rely on methylation status-dependent chemical modification of CpG sequences within isolated genomic DNA, or fragments thereof, followed by DNA sequence analysis. Chemical reagents that are able to distinguish between methylated and non-methylated CpG dinucleotide sequences include hydrazine, which cleaves the nucleic acid, and bisulfite. Bisulfite treatment followed by alkaline hydrolysis specifically converts non-methylated cytosine to uracil, leaving 5-methylcytosine unmodified as described by Olek A., 1996, *Nucleic Acids Res.* 24:5064-6 or Frommer et al., 1992, *Proc. Natl. Acad. Sci. USA* 89:1827-1831, each of which is incorporated herein by reference. The bisulfite-treated DNA can subsequently be analyzed by molecular techniques, such as PCR amplification, sequencing, and detection comprising oligonucleotide hybridization (e.g., using nucleic acid microarrays).

Techniques for the analysis of bisulfite treated DNA can employ methylation-sensitive primers for the analysis of CpG methylation status with isolated genomic DNA, for example, as described by Herman et al., 1996, *Proc. Natl. Acad. Sci. USA* 93:9821-9826, or U.S. Pat. No. 5,786,146 or 6,265,171, each of which is incorporated herein by reference. Methylation sensitive PCR (MSP) allows for the detection of a specific methylated CpG position within, for example, the regulatory region of a gene. The DNA of interest is treated such that methylated and non-methylated cytosines are differentially modified, for example, by bisulfite treatment, in a manner discernible by their hybridization behavior. PCR primers specific to each of the methylated and non-methylated states of the DNA are used in PCR amplification. Products of the amplification reaction are then detected, allowing for the deduction of the methylation status of the CpG position within the genomic DNA. Other methods for the analysis of bisulfite treated DNA include methylation-sensitive single nucleotide primer extension (Ms-SNuPE) (see, for example, Gonzalgo & Jones, 1997; *Nucleic Acids Res.* 25:2529-2531, or U.S. Pat. No. 6,251,594, each of which is incorporated herein by reference), or the use of real time PCR based methods, such as the art-recognized fluorescence-based real-time PCR technique MethyLight™ (see, for example, Eads et al., 1999; *Cancer Res.* 59:2302-2306, U.S. Pat. No. 6,331,393 or Heid et al., 1996, *Genome Res.* 6:986-994, each of which is incorporated herein by reference). It will be understood that a variety of methylation assay methods can be used for the determination of the methylation status of particular genomic CpG positions. Methods which employ bisulfite conversion include, for example, bisulfite sequencing, methylation-specific PCR, methylation-sensitive single nucleotide primer extension (Ms-SnuPE), MALDI mass spectrometry and methylation-specific oligonucleotide arrays, for example, as described in U.S. Pat. No. 7,611,869 or International Patent Application WO2004/051224, each of which is incorporated herein by reference.

In particular embodiments, methylation of genomic CpG positions in a sample can be detected using an array of probes. In such embodiments, a plurality of different probe molecules can be attached to a substrate or otherwise spatially distinguished in an array. Exemplary arrays that can be used in the methods disclosed herein include, without limitation, slide arrays, silicon wafer arrays, liquid arrays, bead-based arrays and others known in the art or set forth in further detail herein. In certain embodiments, the methods disclosed herein can be practiced with array technology that combines a miniaturized array platform, a high level of assay multiplexing, and scalable automation for sample handling and data processing. Particularly useful arrays are described in U.S. Pat. No. 6,355,431; 6,429,027; 6,890,741; 6,913,884 or 7,582,420; or U.S. Pat. App. Pub. Nos. 2002/0102578 A1; 2005/0053980 A1; 2005/0181440 A1; or 2009/0186349 A1, each of which is incorporated herein by reference. Further examples of useful arrays include those described in U.S. Pat. No. 6,023,540, 6,200,737 or 6,327,410; or PCT Pub. Nos. WO9840726, WO9918434 or WO9850782, each of which is incorporated herein by reference.

The plexity of an array used herein can vary depending on the probe composition and desired use of the array. For example, the plexity of nucleic acids (or CpG sites) detected in an array can be at least 10, 100, 1,000, 10,000, 0.1 million, 1 million, 10 million, 100 million or more. Alternatively or additionally, the plexity can be selected to be no more than 100 million, 10 million, 1 million, 0.1 million, 10,000, 1,000, 100 or less. Of course, the plexity can be between one of the lower values and one of the upper values selected from the ranges above. Similar plexity ranges can be achieved using nucleic acid sequencing approaches such as those known in the art as Next Generation or massively parallel sequencing.

A variety of commercially available array-based products for detection of methylation can be used including, for example, the MethylationEPIC™ BeadChip™ (Illumina, Inc., San Diego, Calif.) which allows interrogation of over 850,000 methylation sites quantitatively across a subject's genome at single-nucleotide resolution. Also useful are methylation microarrays available from Agilent (Santa Clara, Calif.) and other commercial suppliers of nucleic acid arrays. The array products can be customized for detection of a wide variety of methylation sites in the animal subject's genome.

Detection of one or more nucleic acids obtained or generated in a technique set forth herein can employ a sequencing procedure, such as a sequencing-by-synthesis (SBS) technique or other techniques known in the art as massively parallel sequencing or Next Generation sequencing. Briefly, SBS can be initiated by contacting the target nucleic acids with one or more labeled nucleotides, DNA polymerase, etc. The target nucleic acid can be derived from a methylation detection technique such as bisulfate conversion or restriction with a methyl sensitive restriction endonuclease. Those features where a primer is extended using the target nucleic acid as template will incorporate a labeled nucleotide that can be detected. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n.

In some embodiments, the methylation level can be determined as the fraction of 'C' bases out of 'C'+'U' total bases at a target CpG site "i" following the bisulfite treatment. In other embodiments, the methylation level can be determined as the fraction of 'C' bases out of 'C'+'T' total bases at site "i" following the bisulfite treatment and subsequent nucleic acid amplification. The mean methylation level at each site is then evaluated to determine if one or more threshold is met. In some embodiments, a threshold selects those sites having the highest-ranked mean methylation values for epigenetic age predictors. For example, the threshold can be those sites having a mean methylation level that is the top 50%, the top 40%, the top 30%, the top 20%, the top 10%, the top 5%, the top 4%, the top 3%, the top 2%, or the top 1% of mean methylation levels across all sites "i" tested for a predictor, e.g., an epigenetic age predictor. Alternatively, the threshold can be those sites having a mean methylation level that is at a percentile rank greater than or equivalent to 50, 60, 70, 80, 90, 95, 96, 97, 98, or 99. In other embodiments, a threshold can be based on the absolute value of the mean methylation level. For instance, the threshold can be those sites having a mean methylation level that is greater than 99%, greater than 98%, greater than 97%, greater than 96%, greater than 95%, greater than 90%, greater than 80%, greater than 70%, greater than 60%, greater than 50%, greater than 40%, greater than 30%, greater than 20%, greater than 10%, greater than 9%, greater than 8%, greater than 7%, greater than 6%, greater than 5%, greater than 4%, greater than 3%, or greater than 2%. The relative and absolute thresholds can be applied to the mean methylation level at each site "i" individually or in combination. As an illustration of a combined threshold application, one may select a subset of sites that are in the top 3% of all sites tested by mean methylation level and also have an absolute mean methylation level of greater than 6%. The result of this selection process is a plurality of epigenetic age predictors, of specific hypermethylated sites (e.g., CpG sites) that are considered the most informative for that age prediction. These lists are then used to identify or classify a test genomic DNA sample from a test animal subject, i.e. to determine the age of the animal subject.

In another method, a test genomic DNA sample from a test animal subject is analyzed by determining the methylation levels at each site "i" on the list of hypermethylated sites for each epigenetic age predictor, and these methylation levels for each predictor are then averaged to calculate the average methylation level across the hypermethylated sites for each age predictor. This process is repeated using the previously defined lists of hypermethylated sites for epigenetic age predictors, and results in a set of average methylation levels for the detecting an animal subject's age.

Analysis of the methylation, prognosis or diagnosis information derived from a method set forth herein can conveniently be performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at an animal facility or shelter and/or media that are not shared with other entities. Examples of indirectly controlled media include media that is indirectly accessible to the user via an external network and/or via a service providing shared resources such as a "cloud." A particularly useful cloud is one that is configured and administered to store and analyze genetic data such as the BaseSpace™ service (Illumina, Inc. San Diego Calif.), or cloud services described in US Pat. App. Pub. Nos. 2013/0275486 A1 or 2014/0214579 A1 (each of which is incorporated herein by reference). Examples of program instructions include both machine code, such as produced by a compiler, and files containing higher level code that may be executed by the computer using an interpreter.

In some embodiments, the data or information employed in the disclosed methods and apparatus is provided in an electronic format. Such data or information may include reads derived from a nucleic acid sample, reference sequences, methylation states, patterns of methylation states, methylation difference scores, normalized methylation difference scores, aggregate coverage-weighted normalized methylation difference scores, methylation scores, coverage-weighted methylation scores, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

In addition, certain embodiments relate to tangible and/or non-transitory computer readable media or computer program products that include instructions and/or data (including data structures) for performing various computer-implemented operations. One or more of the steps of a method set forth herein can be carried out by a computer program that is present in tangible and/or non-transitory computer readable media, or carried out using computer hardware.

For example, a computer program product is provided and it comprises a non-transitory computer readable medium on which is provided program instructions for steps of (a) obtaining a test data set that includes (i) methylation states for a plurality of sites from test genomic DNA from at least one test animal subject, and (ii) coverage at each of the sites for detection of the methylation states; (b) obtaining methylation states for the plurality of sites in reference genomic DNA from one or more reference individual animal subjects, (c) determining, for each of the sites, the methylation difference between the test genomic DNA and the reference genomic DNA, thereby providing a normalized methylation difference for each site; (d) weighting the normalized methylation difference for each site by the coverage at each of the sites, thereby determining an aggregate coverage-weighted normalized methylation difference score, and (e) storing or transmitting the aggregate coverage-weighted normalized methylation difference score.

Methods disclosed herein can also be performed using a computer processing system which is adapted or configured to perform a method for identifying methylation states or other characteristics of nucleic acids. Thus, in one embodiment, the disclosure provides a computer processing system which is adapted or configured to perform a method as described herein. In one embodiment, the apparatus comprises a nucleic acid detection device, such as a nucleic acid sequencing device, adapted or configured to determine methylation states and/or other characteristics of nucleic acids. The apparatus may also include components for processing a sample from a test animal subject and/or reference animal subjects. Such components are described elsewhere herein.

Nucleic acid sequence, methylation state, methylation pattern, or other data, can be inputted into a computer or stored on a computer readable medium either directly or indirectly. In one embodiment, a computer system is directly coupled to a nucleic acid detection device (e.g. sequencing device) that determines methylation states of nucleic acids from samples. Data or other information from such tools are provided via interface in the computer system. Alternatively, the methylation data processed by systems are provided from a data storage source such as a database or other repository. Once available to the processing apparatus, a memory device or mass storage device buffers or stores, at least temporarily, methylation states or other characteristics of the nucleic acids. In addition, the memory device may store methylation differences, normalized methylation differences, aggregate weighted normalized methylation differences, methylation scores, or coverage-weighted methylation scores as described herein. The memory may also store various routines and/or programs for analyzing or presenting such information. Such programs/routines may include programs for performing statistical analyses, etc.

In one example, a user provides a sample to a nucleic acid sequencing apparatus. Data is collected and/or analyzed by the sequencing apparatus which is connected to a computer. Software on the computer allows for data collection and/or analysis. Data can be stored, displayed (e.g., via a monitor or other similar device), and/or sent to another location. The computer may be connected to the internet which is used to transmit data to a handheld device and/or cloud environment utilized by a remote user (e.g., a veterinarian, pet owner, rancher, etc.). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to, a building, city, state, country or continent.

In some embodiments, the methods also include collecting data regarding a plurality of polynucleotide sequences (e.g., reads, tags and/or methylation states) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data that has been collected or stored can be transmitted from the computer to a remote location, e.g., via a local network or a wide area network such as the internet. At the remote location, various operations can be performed on the transmitted data as described below.

Among the types of electronically formatted data that may be stored, transmitted, analyzed, and/or manipulated in systems, apparatus, and methods disclosed herein are the following: reads obtained by sequencing nucleic acids in a test sample, methylation states for sites in the nucleic acids, one or more reference genome or sequence, methylation difference score, normalized methylation difference score, aggregate coverage-weighted normalized methylation difference score, methylation score, coverage-weighted methylation score or age predictor score as described herein.

These various types of data may be obtained, stored, transmitted, analyzed, and/or manipulated at one or more locations using distinct apparatus. The processing options span a wide spectrum. Toward one end of the spectrum, all or much of this information is stored and used at the location where the test sample is processed, e.g., a veterinarian's office, animal shelter, etc. Toward another extreme, the sample is obtained at one location, it is processed (e.g., prepared, detected or sequenced) at a second location, data is analyzed (e.g., sequencing reads are aligned) and methylation characteristics are determined at a third location (or several locations), and diagnoses, recommendations, and/or plans are prepared at a fourth location (or the location where the sample was obtained).

In various embodiments, the methylation data are generated on a nucleic acid detection apparatus (e.g., sequencing apparatus) and then transmitted to a remote site where they are processed to determine methylation characteristics. At this remote location, as an example, methylation difference score, normalized methylation difference score, aggregate coverage-weighted normalized methylation difference score, methylation score, coverage-weighted methylation score, age predictor score can be determined. Also at the remote location, the methylation characteristics can be evaluated to make a prognostic or diagnostic determination.

Any one or more of these operations may be automated as described elsewhere herein. Typically, the detection of nucleic acids and the analyzing of sequence data will be performed computationally. The other operations may be performed manually or automatically.

Examples of locations where sample collection may be performed include veterinarian's offices, animal shelter, zoo, pet or livestock owner's homes (where a sample collection tool or kit is provided). Examples of locations where sample processing prior to methylation detection may be performed include veterinarian's offices, animal shelter, zoo, pet or livestock owner's homes (where a sample processing apparatus or kit is provided), and facilities of nucleic acid analysis providers. Examples of locations where nucleic acid detection (e.g. sequencing) may be performed include veterinarian's offices, animal shelter, zoo, pet or livestock owner's homes, and facilities of nucleic acid analysis providers. The location where the nucleic acid detection takes place may be provided with a dedicated network connection for transmitting sequence data (typically reads) in an electronic format. Such connection may be wired or wireless and may be configured to send the data to a site where the data can be processed and/or aggregated prior to transmission to a processing site.

The analyzing operations may be performed at any of the foregoing locations or alternatively at a further remote site dedicated to computation and/or the service of analyzing nucleic acid sequence data. Such locations include for example, clusters such as general purpose server farms, the facilities of a genetic analysis service business, and the like. In some embodiments, the computational apparatus employed to perform the analysis is leased or rented. The computational resources may be part of an internet accessible collection of processors such as processing resources colloquially known as the "cloud", examples of which are provided elsewhere herein. In some cases, the computations are performed by a parallel or massively parallel group of processors that are affiliated or unaffiliated with one another. The processing may be accomplished using distributed processing such as cluster computing, grid computing, and the like. In such embodiments, a cluster or grid of computational resources collective form a super virtual computer composed of multiple processors or computers acting together to perform the analysis and/or derivation described herein. These technologies as well as more conventional supercomputers may be employed to process sequence data as described herein. Each is a form of parallel computing that relies on processors or computers. In the case of grid computing these processors (often whole computers) are connected by a network (private, public, or the Internet) by a conventional network protocol such as Ethernet. By contrast, a supercomputer has many processors connected by a local high-speed computer bus.

In certain embodiments, the diagnosis (e.g., determination of the age of the animal subject) is generated at the same location as the analyzing operation. In other embodiments, it is performed at a different location. In some examples, reporting the diagnosis is performed at the location where the sample was taken, although this need not be the case.

Examples of locations where the diagnosis can be generated or reported include veterinarian's offices, animal shelter, zoos, and service providers (i.e., companies which perform such services).

In some embodiments, the sample collection, sample processing, and methylation state detection operations are performed at a first location and the analyzing and deriving operation is performed at a second location. However, in some cases, the sample collection is collected at one location (e.g., a veterinarian's office, animal medical hospital, pet owner's home, etc.) and the sample processing and methylation state detecting is performed at a different location (e.g., companies which perform such services).

The following examples are intended to illustrate but not limit the disclosure. While they are typical of those that might be used, other procedures known to those skilled in the art may alternatively be used.

EXAMPLES

Figure 1A:
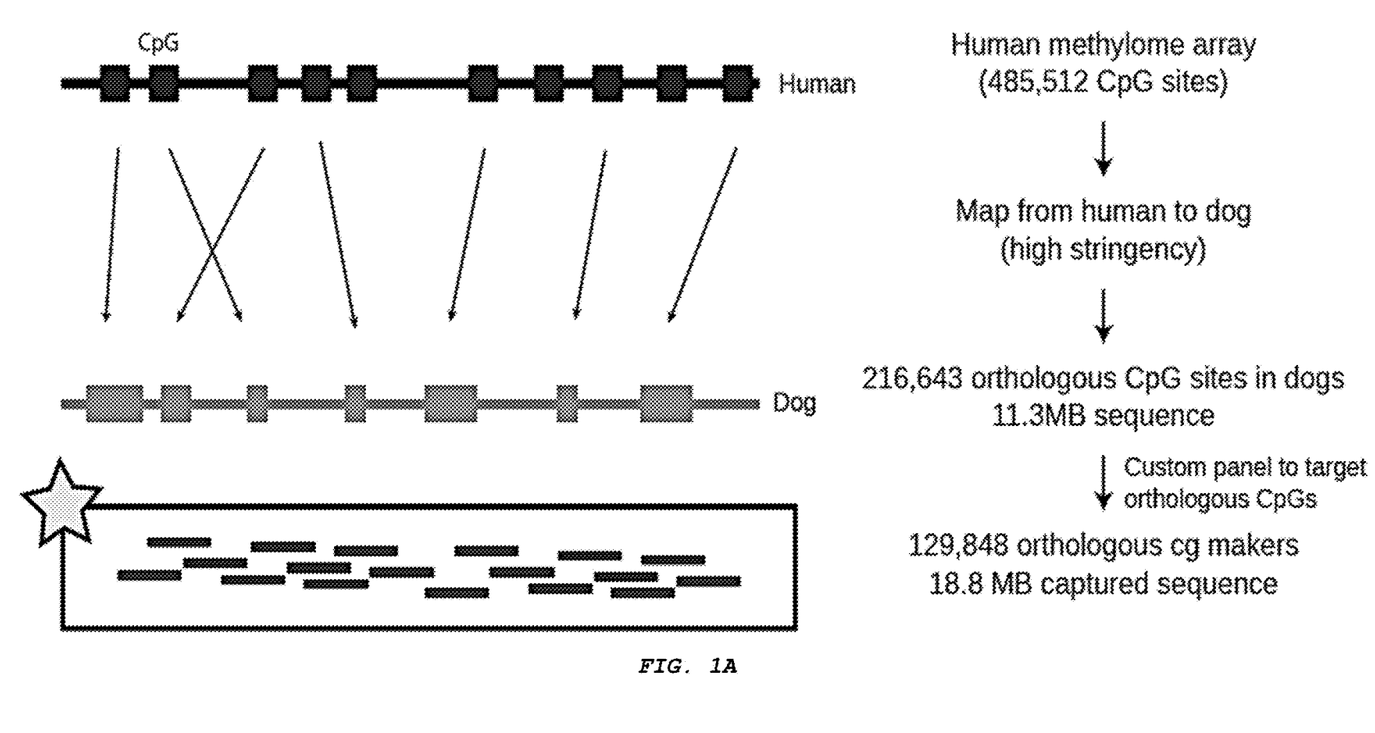
FIG. 1A-C provides a schematic to utilize a canine methylome profiling assay. (A) Selecting regions to profile in dogs based on Illumina human 450K methylation array, in total 129,848 CpGs can be compared between human and dogs. (B) General workflow to generate captured methylome data and compare to humans in 2 general analysis steps. (C) Training an epigenetic-age predictor in 3 general analysis steps. For (B) and (C), colors match those outlined in (A). (QC: Quality control).
Figure 1B:
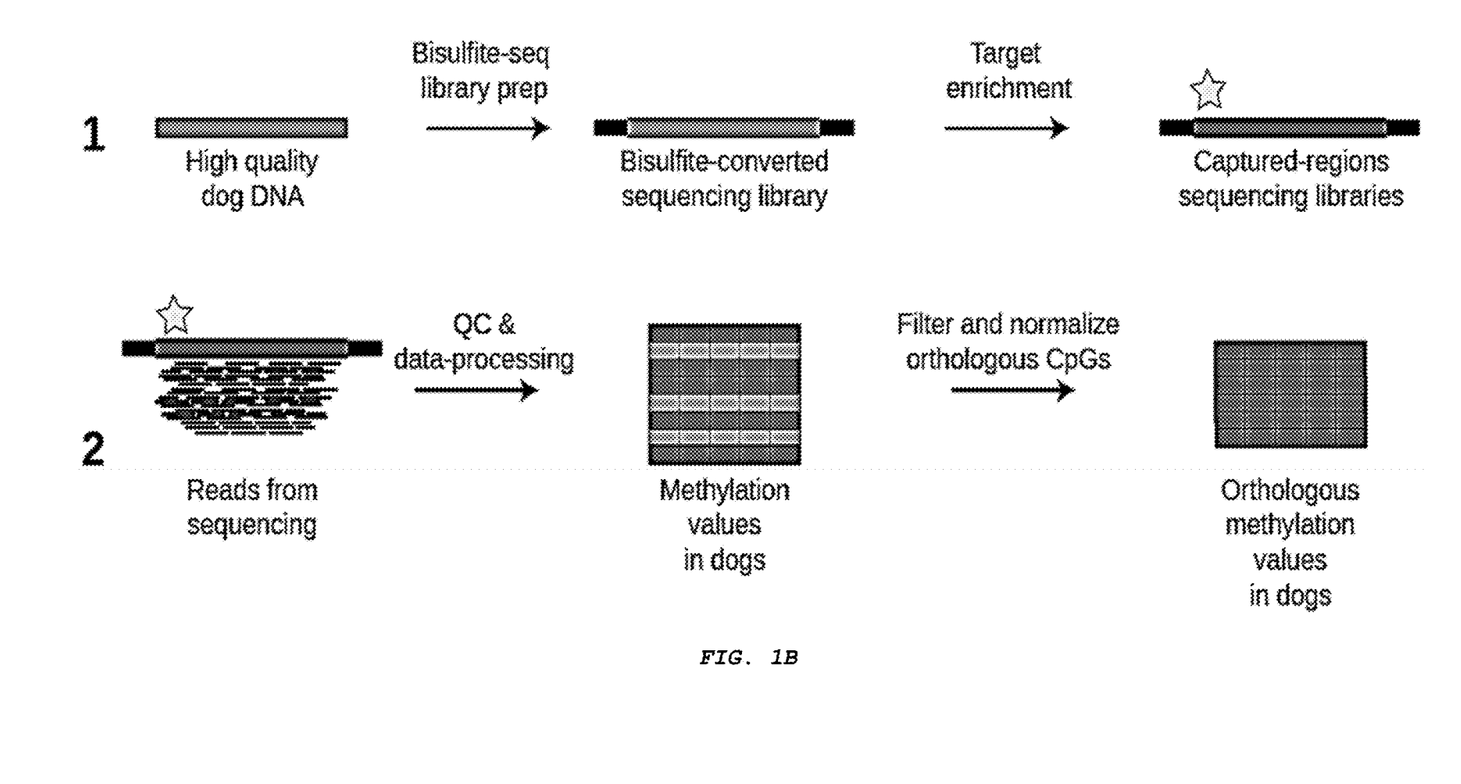
Figure 1C:
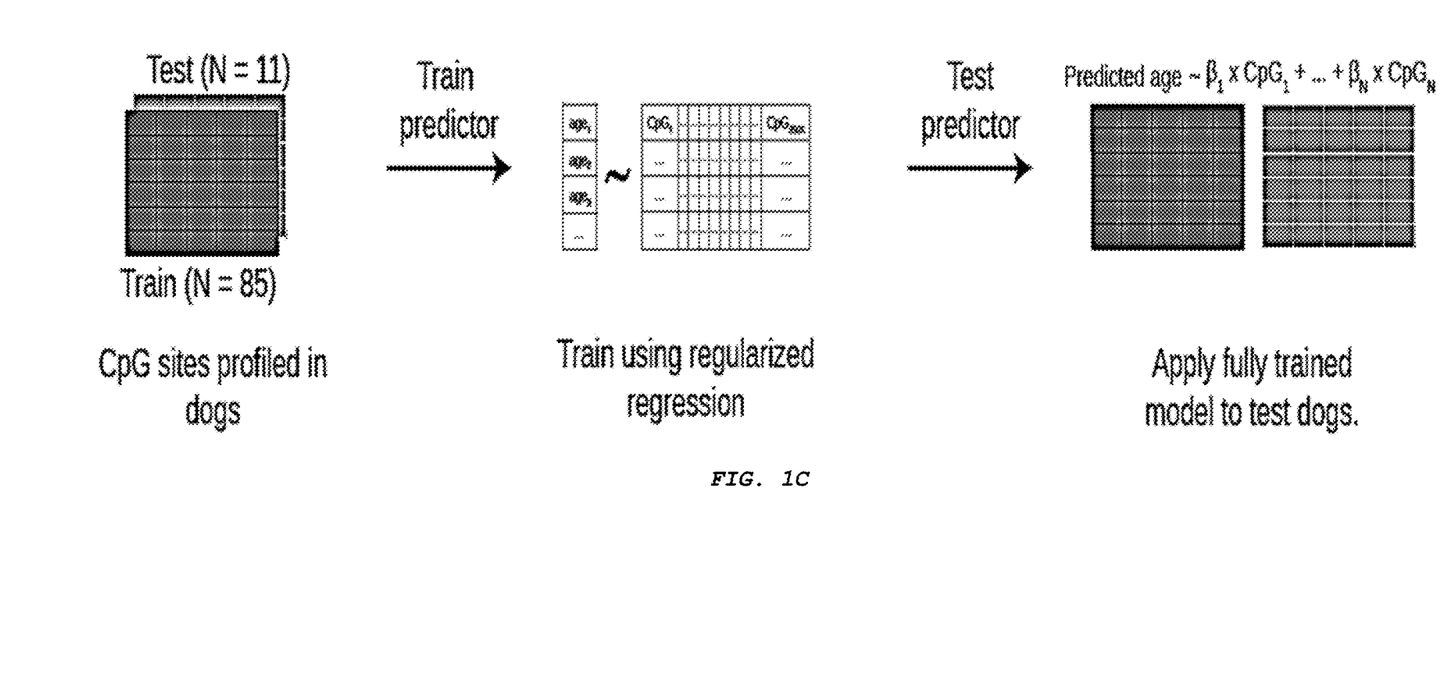
Figure 2A:
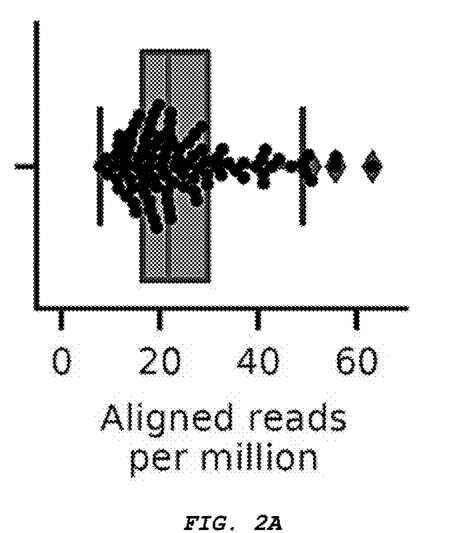
FIG. 2A-D presents alignment statistics for a targeted dog methylome assay. After quality control and alignment of captured sequencing reads to the dog genome (96 samples), millions of reads were then aligned (A) resulting in an on-target rate between 30-60% (B). The average coverage of sites between 12× to 200× in 54,469 orthologous CpG sites measured in both human and dog (C), and 6× to 119× in 304,491 CpG sites in dogs (D).
Figure 2B:
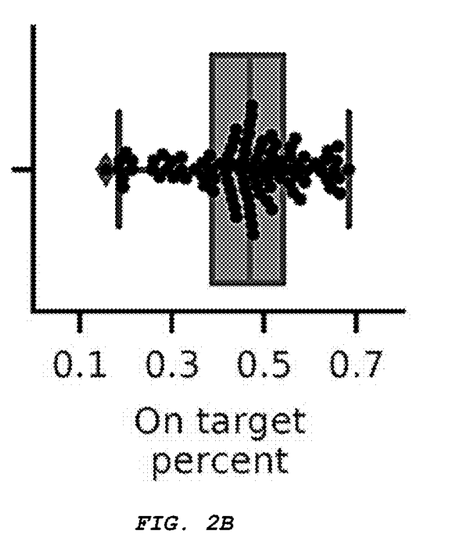
Figure 2C:
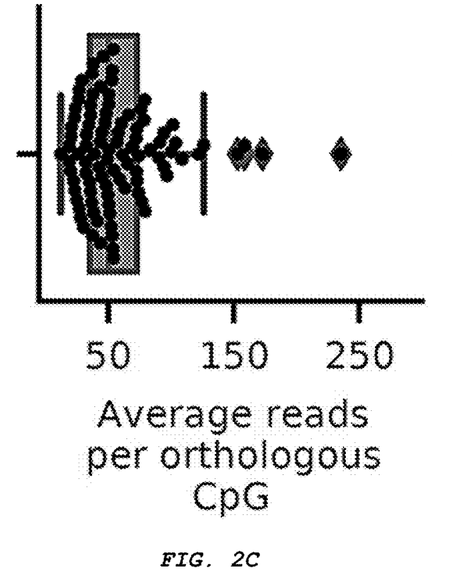
Figure 2D:
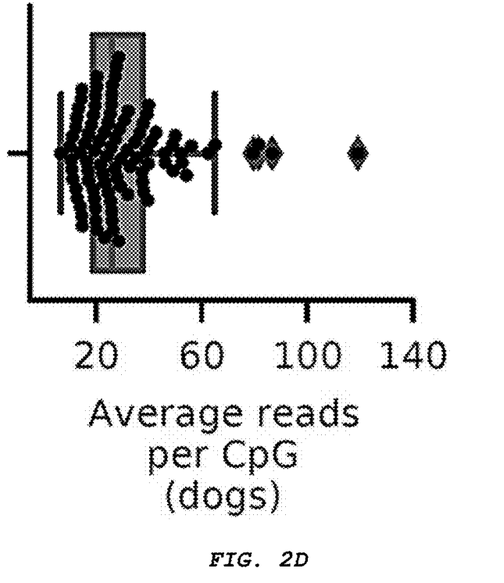
Figure 3A:
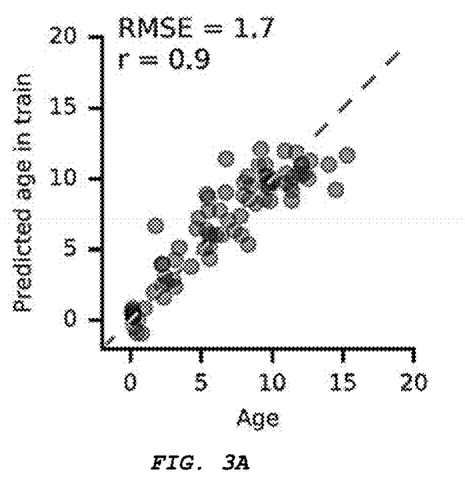
FIG. 3A-C presents epigenetic-age predictor performance. An epigenetic-age predictor was trained on CpGs present in dogs. (A) The performance of the fully trained-model on training data. (B) The performance of the fully trained-model in 5-fold cross validation (CV) in the training data, with the error and Pearson's correlation shown. (C) The performance of the fully-trained model using dog methylome data in 17 total samples, where 11 unique dogs were with-held from training, and 6 of the 11 are technical replicates. (RMSE: Root mean squared error, r: Pearson's correlation)
Figure 3B:
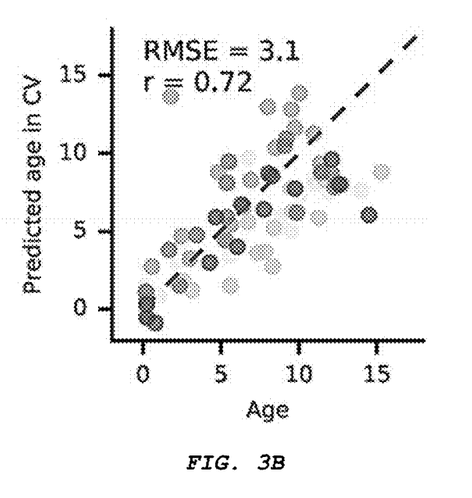
Figure 3C:
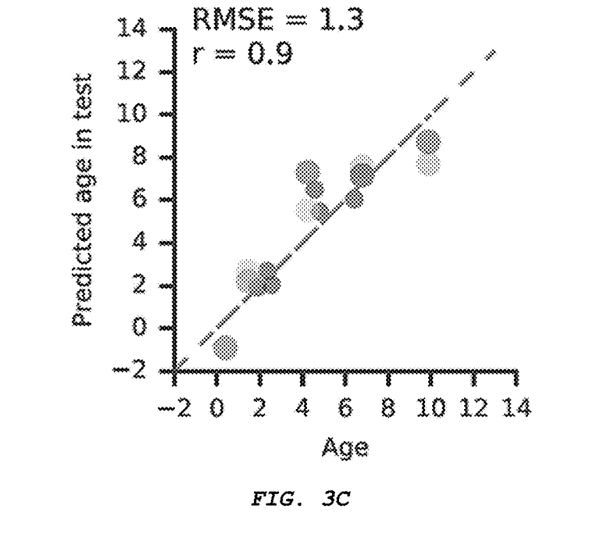

Isolation and extraction of cfDNA from Plasma. Plasma samples are obtained from animal blood draws. Cell free DNA (cfDNA) was extracted using the QIAamp Circulating Nucleic Acid Kit (Qiagen, Hilden, Germany). Targeted ctDNA methylation sequencing was carried out according to the workflow shown in FIG. 1, and as set forth below in the context of evaluating titration and detection sensitivity.

Bisulfite treatment of cfDNA and array capture. Extracted cfDNA or sheared and size-selected genomic DNA is bisulfite treated and purified using EZ DNA Methylation-Lightning Kit (Zymo Research, Irvine, Calif.). Bisulfite-seq Libraries can be prepared using the Accel-NGS® Methyl-Seq DNA Library Kit (Swift Biosciences, Ann Arbor, Mich.). Targeted capture can be carried out on the bisulfite-seq libraries using probes that were complementary to fragments having CpG sites. Capture probes were synthesized and biotinylated at Illumina, Inc. Target capture can be performed using Illumina TruSight™ Rapid Capture Kit according to manufacturer's instructions or modifications thereof. The products of the capture step can be sequenced on an Illumina HiSeq 4000 Sequencer using 2×100 cycle runs, with four samples in rapid run mode, according to manufacturer's instructions.

Bioinformatic Analysis. FASTQ sequences can demultiplexed followed by in silico demethylation whereby all C's on read 1 were converted to T's and all G's on read 2 are converted to A's. Subsequently, these "demethylated" FASTQ sequences are aligned using BWA (v 0.7.10-r789) to an index comprising a "demethylated" genome. BWA alignment is described in Li and Durbin (2010) Fast and accurate long-read alignment with Burrows-Wheeler Transform. Bioinformatics, Epub. [PMID: 20080505], which is incorporated herein by reference. Following alignment, the "demethylated" FASTQ sequences are replaced with the original FASTQ sequences. Methylation levels are calculated as the fraction of 'C' bases at a target CpG site out of 'C'+'T' total bases. Following calculation of methylation levels at each CpG site for each sample and replicate, aggregate coverage-weighted normalized methylation difference z-scores can be calculated. The methylation level at each CpG site can be normalized by subtracting the mean methylation level in baseline and dividing by the standard deviation of methylation levels in baseline to obtain a per-site z-score. The z-score at each CpG site is then multiplied by the coverage observed at the CpG site, and the coverage-weighted z-score is then summed across all CpG sites and then divided by the sum of the coverage squared at each CpG site.

Methylome profiling in dogs. 96 canines were tested in the assay. DNA was extracted from blood, assessed for quality (i.e., no heavy degradation) and quantified using fluorescence based measurements. The DNA was then subjected to whole-genome-bisulfite library preparation using Kapa library construction kits. This process involved shearing DNA to 100-500 bp fragments, ligating methylated sequencing adapters and bisulfite-treating with Zymo EZ DNA methylation kit. The sequencing libraries were then quantified and hybridized to the SeqCap capture probes, multiplexing 6 to 12 dogs to one capture reaction. Successfully captured libraries were then PCR amplified using the sequence of ligated adapters and sequenced with 2×100 bp reads on an Illumina HiSeq 4000, yielding a total of 590 million reads across all samples.

Results of sequencing were de-multiplexed and analyzed using custom scripts. Sequencing results were aligned using bowtie2 that was specialized for bisulfite-conversion. A bisulfite conversion of >99.5% was achieved for all samples. The reads were on average ~58% on target, yielding an average coverage of ~99.8% of uniquely targeted regions across all samples. This sequencing provided coverage of X total million CpGs that were present in >90% of samples, where >300,000 had at least 5× coverage, wherein X is any value from 10,000 to several million (e.g., 20,000, 100,000, 200,000, 500,000, 1,000,000, 1.5 million, 1.8 million, 2 million etc.). This allowed the assessment of high-quality CpGs between human and dog. This assay represents the largest syntenic methylation study between human and species that are distantly related (>50 million years).

DNA methylation as a quantitative predictor of age in dogs. DNA was extracted from blood, assessed for quality (i.e., no heavy degradation) and quantified using fluorescence based measurements. The DNA was then subjected to whole-genome-bisulfite library preparation using Kapa library construction kits. This process involved shearing DNA to 100-500 bp fragments, ligating methylated sequencing adapters and bisulfite-treating with Zymo EZ DNA methylation kit. The sequencing libraries were then quantified and hybridized to the SeqCap capture probes, multiplexing 6 to 12 dogs to one capture reaction. Successfully captured libraries were then PCR amplified using the sequence of ligated adapters and sequenced with 2×100 bp reads on an Illumina HiSeq 4000, yielding a total of 2390 million aligned reads across all samples.

Results of sequencing were de-multiplexed and analyzed using custom scripts. Sequencing results were aligned using bowtie2 that was specialized for bisulfite-conversion. A bisulfite conversion of >99.5% was achieved for all samples. The reads were on average ~46% on target, yielding an average coverage of ~99.3% of uniquely targeted regions across all samples. This sequencing provided coverage of 2.9 million CpGs that were present in 90% of samples, where 304,191 had at least 5× coverage. This allowed the assessment of 54,469 high-quality CpGs between human and dog.

A predictor of age was trained using dog methylation data using machine learning methods, specifically an ElasticNet regression framework in 85 dogs. The most optimal parameters were selected using 5-fold cross-validation, then tested on a total of 16 samples, consisting of 11 unique dogs and 5 technical replicates. It was found that the average error between predicted age and actual age in the cohort was 1.2 years with a Pearson's correlation of 0.9. Thus, the performance of this trained epigenetic predictor is very accurate and is an improvement on teeth estimates for ages >1 years old.

It will be understood that various modifications may be made without departing from the spirit and scope of this disclosure. Accordingly, other embodiments are within the scope of the following claims.

What is claimed is:

1. A method of generating a methylome profile of a canine subject, the method comprising:
isolating and fractioning genomic DNA (gDNA) from a canine subject to form gDNA fragments;
treating the gDNA fragments with bisulfite to convert unmethylated cytosines into uracils;
capturing bisulfite treated gDNA fragments having CpG sites with capture probes having a sequence complementary to bisulfite treated gDNA fragments, wherein the capture probes that target genetic loci having a genomic location selected from the following:

| | Genomic location | |
|---|---|---|
| chromosome | start | end |
| 10 | 32155572 | 32155573 |
| 10 | 47400603 | 47400604 |
| 11 | 12143642 | 12143643 |
| 1 | 113745958 | 113745959 |
| 11 | 56810628 | 56810629 |
| 11 | 56810721 | 56810722 |
| 12 | 63488774 | 63488775 |
| 14 | 22067955 | 22067956 |
| 14 | 40131029 | 40131030 |
| 14 | 40366402 | 40366403 |
| 16 | 46562076 | 46562077 |
| 16 | 53697863 | 53697864 |
| 16 | 53697881 | 53697882 |
| 17 | 62480024 | 62480025 |
| 21 | 27195140 | 27195141 |
| 21 | 27396898 | 27396899 |
| 22 | 1780265 | 1780266 |
| 23 | 42484424 | 42484425 |
| 24 | 36795647 | 36795648 |
| 25 | 5057162 | 5057163 |
| 25 | 5057174 | 5057175 |
| 26 | 5250703 | 5250704 |
| 26 | 5330973 | 5330974 |
| 26 | 5330978 | 5330979 |
| 26 | 5330998 | 5330999 |
| 26 | 5331204 | 5331205 |
| 26 | 5331230 | 5331231 |
| 28 | 38491744 | 38491745 |
| 30 | 14008101 | 14008102 |
| 3 | 15906095 | 15906096 |
| 3 | 15906160 | 15906161 |
| 32 | 30355909 | 30355910 |
| 33 | 25412867 | 25412868 |
| 34 | 7326879 | 7326880 |
| 37 | 22520990 | 22520991 |
| 38 | 18152079 | 18152080 |
| 38 | 18152126 | 18152127 |
| 38 | 18152133 | 18152134 |
| 5 | 29282901 | 29282902 |
| 5 | 32970662 | 32970663 |
| 5 | 32970672 | 32970673 |
| 5 | 48883108 | 48883109 |
| 5 | 48883118 | 48883119 |
| 5 | 67246847 | 67246848 |
| 5 | 79537151 | 79537152 |
| 7 | 80969482 | 80969483 |
| 9 | 19960393 | 19960394 |
| 9 | 20510871 | 20510872 |
| 9 | 24868907 | 24868908 |
| 9 | 24868926 | 24868927 |
| 9 | 24869027 | 24869028 | wherein the capture probes further comprise methylated sequencing adaptors, and
wherein the CpG sites of the bisulfite treated gDNA fragments are orthologous between humans and canines;
amplifying and sequencing the capture gDNA fragments to generate sequencing reads of the canine subject; and
generating the methylome profile of the canine subject from the sequencing reads.

2. The method of claim 1, wherein the capture probes target 1-10,000 orthologous CPG sites between humans and canines.

* * * * *